(12) United States Patent
McAffer et al.

(10) Patent No.: US 9,168,201 B2
(45) Date of Patent: Oct. 27, 2015

(54) AMPOULES

(75) Inventors: Ian Gardener Cameron McAffer, Kent (GB); Peter Ernest Tasko, Kent (GB)

(73) Assignee: Breath Ltd., Kent (GB)

(*) Notice: Subject to any disclaimer, the term of this patent is extended or adjusted under 35 U.S.C. 154(b) by 440 days.

(21) Appl. No.: 13/598,738

(22) Filed: Aug. 30, 2012

(65) Prior Publication Data

US 2013/0012910 A1 Jan. 10, 2013

Related U.S. Application Data

(63) Continuation of application No. 12/514,725, filed as application No. PCT/GB2007/004476 on Nov. 22, 2007, now Pat. No. 8,277,433.

(30) Foreign Application Priority Data

Nov. 22, 2006 (GB) .................................. 0623320.9
May 15, 2007 (GB) .................................. 0709273.7

(51) Int. Cl.
*A61J 1/06* (2006.01)
*A61J 1/14* (2006.01)

(52) U.S. Cl.
CPC ................ *A61J 1/067* (2013.01); *A61J 1/1443* (2013.01)

(58) Field of Classification Search
CPC ................................ A61J 1/067; A61J 1/1443
USPC ........... 604/403, 406, 410; 222/188; 137/144, 137/544
See application file for complete search history.

(56) References Cited

U.S. PATENT DOCUMENTS

| 4,230,582 A | 10/1980 | Tuleja |
| 4,491,245 A * | 1/1985 | Jamison ........................ 222/107 |
| 5,018,646 A | 5/1991 | Billman et al. |
| 5,478,337 A | 12/1995 | Okamoto et al. |
| 2004/0182883 A1 | 9/2004 | Weiler |
| 2006/0108384 A1* | 5/2006 | Zahn et al. ................. 222/541.9 |
| 2006/0163109 A1 | 7/2006 | Hansen |
| 2006/0177610 A1 | 8/2006 | McAffer et al. |
| 2008/0257481 A1 | 10/2008 | McAffer et al. |

FOREIGN PATENT DOCUMENTS

| WO | 03/094680 A1 | 11/2003 |
| WO | 2006/058139 A2 | 6/2006 |
| WO | 2006085063 | 8/2006 |

OTHER PUBLICATIONS

International Search Report and Written Opinion for International Application No. PCT/GB2007/004476, filed on Nov. 22, 2007, mailed on Jun. 2, 2008, European Patent Office, Rijswijk, Netherlands.
Search Report for United Kingdom Application No. GB0623320.9, completed on Mar. 19, 2007, European Patent Office, Newport, South Wales.

* cited by examiner

*Primary Examiner* — Leslie Deak
(74) *Attorney, Agent, or Firm* — Florek & Endres PLLC

(57) ABSTRACT

An ampoule made of plastics material, for liquid or suspension pharmaceuticals, has a reservoir linked to a removable head by a channel in a neck portion. The channel has a trap, thus located between its reservoir and the head, in the form of an elongated restriction and/or a bend to trap liquid or suspension which may settle during storage, and prevent either reaching the head.

16 Claims, 5 Drawing Sheets

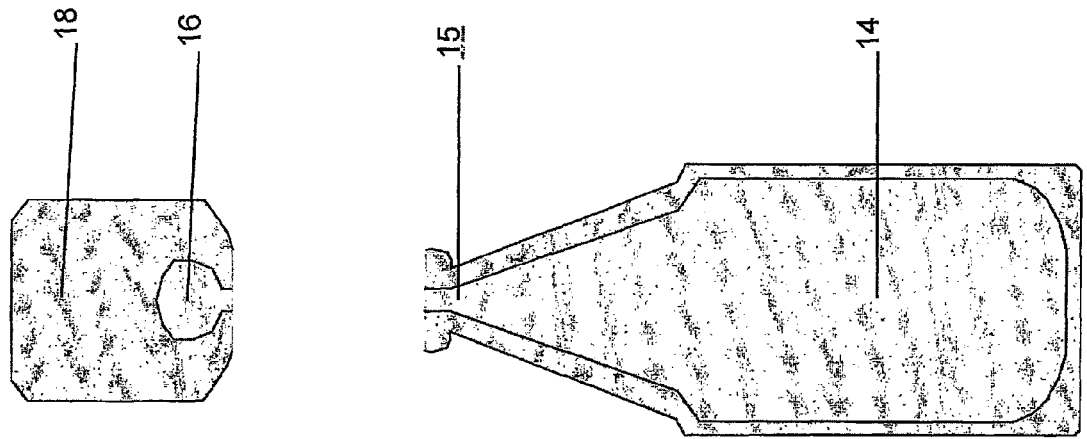
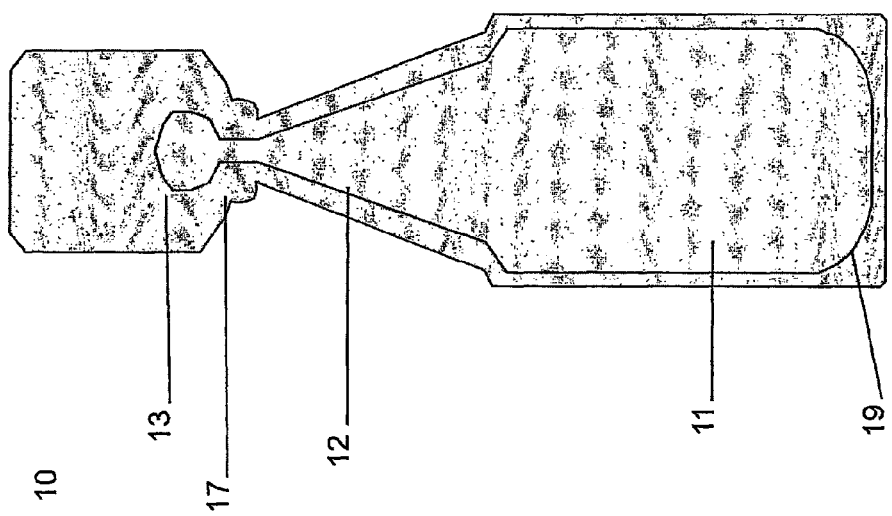

AMPOULES

This application is a continuation of U.S. patent application Ser. No. 12/514,725 filed Jun. 23, 2009, which is the U.S. national stage filing under 35 U.S.C. §371 of International Application No PCT/GB07/04476 filed Nov. 22, 2007, which in turn claims priority to Great Britain application No. 0709273.7 filed May. 15, 2007 and Great Britain application No. 0623320.9 filed Nov. 22, 2006.

FIELD OF THE INVENTION

The present invention relates to liquid containers for suspensions, generally made of plastics material by blow-fill-seal methods. In particular the invention relates to plastic ampoules containing suspensions of pharmaceutical agents for use in nebulisers or as nose drops.

BACKGROUND OF THE INVENTION

Liquids can be filled and packaged in a variety of different containers, including ampoules made from glass or plastic.

Traditionally, glass has been the predominant packaging material for sterile pharmaceutical liquids; however, aseptic processing, involving filling open glass bottles or phials, sets high demands on the manufacturer to obtain aseptic conditions at all times, especially for large-volume containers.

Handling of glass containers always involves a certain risk for lacerations and glass splinters. It has also been shown that glass ampoules generate a fine array of small glass particles during opening. The sub-atmospheric pressure inside the ampoule tends to draw such particles inside the ampoule on opening. US 2006/0163109 describes an ampoule with an air entry port in the neck intended to assist with the reliable filling of a syringe or needle base.

Single doses of liquid products such as pharmaceuticals are now frequently packaged in plastic ampoules. The user is required to open one end of the ampoule in order to access the product. To facilitate this, the body of an ampoule, which forms the reservoir for the contents, typically narrows towards the top to form a neck which then widens once more to form a cul-de-sac or bulb in the head. The neck and head are designed to allow the head to be easily detached by breaking or tearing of the neck along a tear line, providing an opening for the flow of product from the body of the ampoule via a channel in the neck. The present invention relates especially to such ampoules.

Pharmaceutical suspensions contain ingredients which are undissolved within a carrier liquid and thus prone to settling on the bottom or sides of the ampoule during storage. If the ampoules are inverted or stored upside-down settled suspension may pass down the neck into the head of the ampoule. In certain ampoules the narrowing of the flow path between the head and the neck is such that even once the ampoule is upright the surface tension of the liquid is sufficient to hold the suspension within the head. Thus, when the user detaches the head of the ampoule, an amount of product, whether liquid containing suspension or settled suspension, is retained within the head and thus a portion of the suspension is lost and not delivered to the patient.

The amount of suspension, i.e. active ingredient, in such pharmaceutical compositions may be very low with respect to the volume of liquid. Thus the proportion of the suspension that can settle in or around the head may be high, so loss of suspension in this way can be highly significant, resulting in significant reduced effectiveness of the medication.

A related problem is that ampoule contents retained within the head may on opening be transferred to the fingers of the patient and may lead to further transfer for example onto the eyes or the face of the patient if the pharmaceutical is not washed off the fingers immediately. This problem applies to both solution and suspension pharmaceuticals in plastic ampoules.

An option is to enlarge the diameter of the flow path between the neck and the head so that liquid is not retained in the head and so that once the ampoule is correctly orientated the liquid returns to the reservoir. However, while the ampoule was upside-down the active ingredient of the suspension may have settled in the head and may remain there. Thus, when the user dispenses the medication the volume may appear to be correct and it would not be apparent that a portion of the active ingredient would be lost when the head is detached.

US 2004/0182883 describes a hermetically sealed container with a constriction in the neck intended to eliminate any dripping or splashing when the cap is removed along a tear line. A problem, however, with this container is that the constriction may not prevent settled suspension passing into the head. A further problem is that dispensing of the container contents is made difficult by the narrowness of the constriction. In addition, formation of such narrow constrictions is not easily and reliably achievable, and hence this type of container is not practical to make on a large scale for pharmaceutical uses or may require expensive modification of existing machinery.

An object of the present invention is to solve or at least ameliorate the above-identified issues. An object of preferred embodiments of the invention is to provide plastics ampoules which retain less suspension in their head portions after inversion during storage.

SUMMARY OF THE INVENTION

The invention is based upon modification of ampoules, especially of the neck portion of ampoules, to retain active ingredient within the body of the ampoule and/or to reduced or prevent settling of suspension within the head.

In a first aspect, the invention provides an ampoule, comprising:—
(i) a body comprising a reservoir for up to 50 ml of liquid;
(ii) a removable head portion; and
(iii) a neck portion, linking the body to the head, comprising a channel through which liquid in the reservoir can exit the ampoule when the head has been removed, wherein the neck portion comprises a trap to prevent suspended particles in the liquid which have settled from reaching the head.

In a second aspect, the invention provides an ampoule, comprising:—
(i) a body comprising a reservoir for up to 50 ml of liquid;
(ii) a removable head portion; and
(iii) a neck portion, linking the body to the head, comprising a channel through which liquid in the reservoir can exit the ampoule when the head has been removed, wherein the neck portion comprises a trap to prevent the liquid from reaching the head.

In a further aspect, this present invention prevents or at least reduces the loss of solids from the ampoule when it is opened. An ampoule of this aspect comprises a particulate trap which prevents the solids from reaching the part of the ampoule that is discarded on opening.

The invention also provides a method of making an ampoule, the ampoule comprising a reservoir for up to 50 ml of liquid, a removable head portion and a neck portion having a channel for exit of liquid from the reservoir when the head has been removed, the method comprising:—

(i) moulding plastics material into the form of an ampoule;
(ii) injecting liquid into the ampoule;
(iii) providing, in the neck of the ampoule, a trap to prevent suspended particles in the liquid which have settled from reaching the head or a trap to prevent liquid from reaching the head.

DETAILED DESCRIPTION OF THE INVENTION

An ampoule of the invention comprises a body comprising a reservoir for up to 50 ml of liquid; a removable head portion; and a neck portion, linking the body to the head, comprising a channel through which liquid in the reservoir can exit the ampoule when the head has been removed, wherein the neck portion comprises a trap to prevent suspended particles in the liquid which have settled from reaching the head. The trap may also prevent liquid from reaching the head.

The trap is generally formed in or by the channel in the neck portion, thus forming an integral part of the ampoule. It is optional for the trap to be so designed that not only does no suspension reach the head during storage, but neither does any of the contents of the ampoule. Thus in embodiments of the invention there is provided an ampoule wherein the trap prevents liquid from reaching the head portion. To achieve this the neck portion may be designed to be of reduced diameter so that a combination of air in the head and surface tension prevents liquid from reaching all the way up the neck into the head, even when the ampoule is inverted or agitated, or both.

One suitable trap is formed by a restriction in the neck portion. The diameter of the neck must be sufficient to enable ampoule contents to be emptied. But, the neck can be restricted so as to allow the contents to be emptied but so that a combination of surface tension and back pressure from air in the head portion means that during inversion or agitation liquid is substantially prevented from passing the restriction. The restriction is preferably formed along substantially the length of the neck. In embodiments of the inventions described in an example below, an ampoule comprises an elongated, restricted channel in the neck, forming a trap substantially preventing liquid reaching the head during inversion of a filled ampoule.

The elongated, restricted channel in the neck of the ampoule of the present invention is generally at least 1/10, typically at least 1/5 and further generally up to 3/4 of the length of the reservoir within the ampoule body.

Further, in embodiments of the invention, the length of the restricted channel is 3 mm or more, 4 mm or more and generally 5 mm or more. Preferably the length of the channel is 7 mm or more and can be 10 mm or more, e.g. from about 10 to about 15 mm or 15 mm or more, e.g. from about 15 mm to about 25 mm.

The diameter of the elongated restricted channel of the neck of the ampoule of the present invention is generally less than 1/4, typically less than 1/6 of the diameter of the reservoir inside the ampoule body.

Further, in embodiments of the invention the restricted channel typically has a diameter of 3 mm or less, or 2 mm or less, preferably in the range 0.7-3 mm or 0.7-2 mm, and can be from about 1 to about 1.5 mm or from about 1.5 to about 2.5 mm.

An advantage of the elongated, restricted neck channel is that it is sufficiently wide that ease of dispensing is not unacceptably compromised whilst having a combination of narrowness and length sufficient to act as a trap. The channel is of a width that can be easily and reliably formed in mass manufactured plastics ampoules.

Another suitable trap is a bend in the channel of at least 45 degrees. Settled material does not pass easily around the bend and is hence prevented from reaching the head. The bend is preferably at least 75 degrees, more preferably at least 90 degrees.

The channel may suitably be in the form of or comprise a U-bend; again, this bend creating an obstacle through which settled suspension must pass in order to reach the head. Settled suspension which is located in this U-bend, or in other bends, may be re-suspended upon agitation of the ampoule and returned to the reservoir. Alternatively, when the ampoule is opened, drug contained in settled suspension which is located in the bend, and which does not re-suspend upon agitation of the ampoule and is thus not returned to the reservoir, will be flushed out by the reservoir contents passing through the bend, thus ensuring the total contents of the drug within the suspension is delivered. The bend can have a C-shaped, S-shaped or Z-shaped form, it being appreciated with respect to these definitions that the sides of the channel are generally rounded and that these definitions represent the approximate shapes of the channel when viewed from the side.

In further embodiments of the invention the channel comprises two bends, which may both be U-bends.

In still further embodiments the channel comprises an elongated substantially curved neck portion, optionally incorporating one or more bends as described above.

In particularly preferred embodiments of the invention described in the examples below, containers comprise an elongated, restricted channel having at least one bend.

The invention relates additionally to manufacture of ampoules, and thus provides a method of making an ampoule, the ampoule comprising a reservoir for up to 50 ml of liquid, a removable head portion and a neck portion having a channel for exit of liquid from the reservoir when the head has been removed, the method comprising:—
  moulding plastics material into the form of an ampoule;
  filling the ampoule with liquid;
  providing, in the neck of the ampoule, a trap to prevent suspended particles in the liquid which have settled from reaching the head.

Optional and preferred features of the ampoules made by the method are as for the embodiments of the invention described elsewhere herein.

The invention relates in particular to small volume ampoules, thus in preferred embodiments the reservoir contains up to 10 ml of liquid, more preferably up to 5 ml of liquid.

The invention further relates in particular to ampoules containing a suspension of a pharmaceutical, for example a suspension of a steroid, for example budesonide, mometasone, fluticasone, beclomethasone and triamcinolone (including where appropriate compounds of the same such as propionates and furoates).

The ampoules are preferably made of plastics material, in particular plastics material which comprises polyethlene or polypropylene.

The ampoules are particularly suitable for delivery of suspensions by nebulisation.

An advantage of embodiments of the invention that is readily appreciated is that less suspension settles in the head and hence less suspension is lost when head is removed, possibly none is lost. When ampoules are inverted or shaken in storage suspension which settles and which might otherwise reach the head is trapped in the neck portion. When the ampoule is opened this settled suspension is not lost and the patient does not risk receiving less than a full dose. Instead when the ampoule contents are emptied into a nebuliser the settled suspension in the trap is washed out by the ampoule liquid. Suspension trapped as described may be more easily re-suspended and returned to the reservoir. There is less or no need for a "store upright" precaution on the packaging.

Ampoules of the invention are very suitably made using blow-fill-seal, a specialised packaging technology using in-line forming and sealing of a polymeric material to a container of choice. A known blow-fill-seal machine includes a polymer granule storage and feeding system; a rotating screw extruder with parison head; a sterile air-filling chamber; mould halves to form and close the container; and downstream equipment including, for example, leak-detecting systems. Traditional aseptic processing equipment, such as stainless-steel tanks and sterile filters, ensures that the blow-fill-seal machine is fed with sterile liquid. Polymer granules are fed via a vacuum tubing system into the hopper of the blow-fill-seal extruder, where they are heated to form a melt (160-170 degrees C.). The homogeneous polymer melt is formed via a circular orifice into a plastic parison (hollow tube), which is prevented from collapse by a stream of sterile filtered air. The lower part of the divided mould halves can now close to seal the bottom of the open parison and the parison wall is blown and/or sucked to the cooled mould walls to form the lower part of the container. Filling needles draw the stipulated volume of product into the container and, after withdrawal of the filling needles, the upper part of the mould closes to form and seal the upper part of the blow-fill-seal container. Thus, the forming, filling and sealing steps have been made in one unit operation, the cycle generally being completed within 12 to 17 seconds.

The typical materials used in blow-fill-seal processing are or comprise polyethylene or polypropylene. Both are considered inert and give a good balance of properties, enabling easy forming, opening and handling of the finished container.

Blow-fill-seal contract services are operated by several companies, including Cardinal Health Sterile Technologies (IL, USA), Holopack USA, Inc, Holopack (Germany) and Unither (France).

The invention is now further described in specific embodiments with reference to the accompanying drawings in which:—

FIG. 1 shows a side view of a prior art ampoule, intact (1a) and with the head removed (1b);

EXAMPLES

Figure 2:
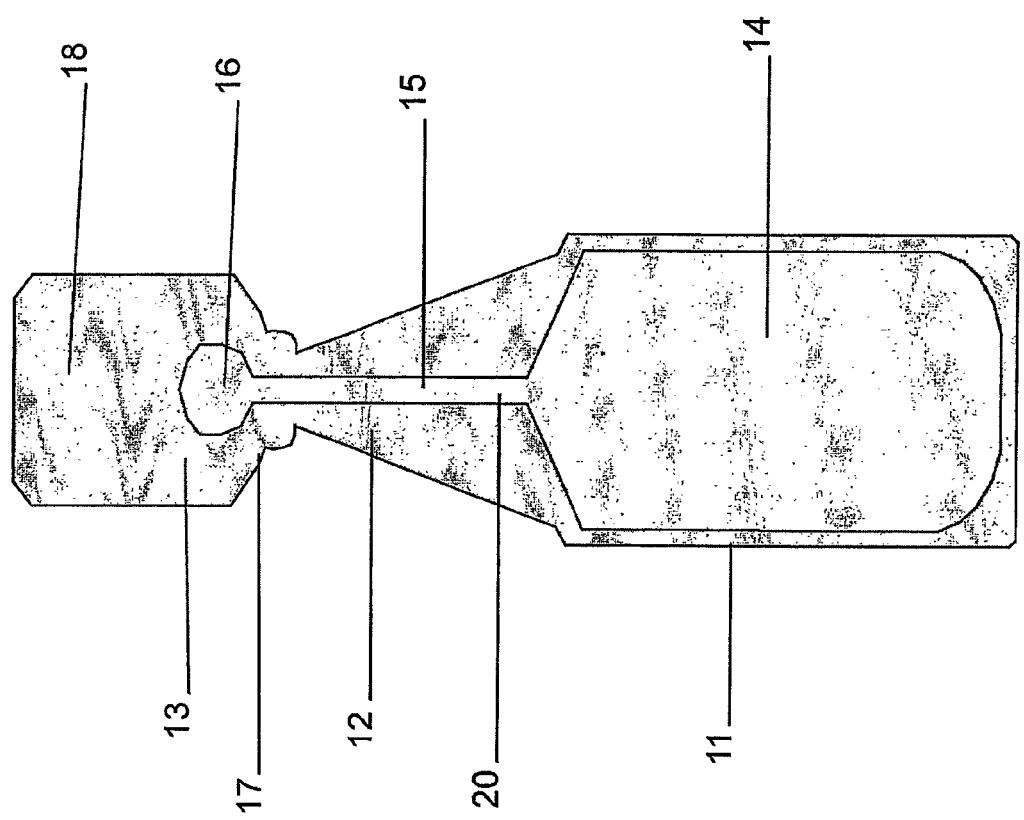
FIG. 2 shows a schematic cross-section of an ampoule of the invention, not including the base portion.

Referring to FIGS. 1, 2, 3, 4 and 5, an ampoule (10) has a body (11) connected by neck (12) to a head portion (13). A reservoir (14) inside the body contains a suspension of a pharmaceutical. There is a channel (15) linking the reservoir to a bulb (16) in the head.

To empty the contents of the ampoule, a patient tears the head from the body along weakened tear-line (17). The combination of the tear line and the bulb tends to ensure that the ampoule tears open fairly cleanly along the tear line. The patient discards the head and empties the contents of the reservoir through the channel.

The head may also have a tab (18) onto which a label can be applied. There may also be a further tab (not present in this case) forming an extension from the base (19).

Referring specifically to FIG. 2, the channel (15) has a restriction (20) along substantially all of its length. The channel is additionally elongated compared with the prior art channel. In use, when the ampoule is inverted or shaken it is found that liquid in the reservoir cannot advance up the restriction all the way to the bulb (16). As shown in FIG. 2, the bulb (16) comprises a diameter greater than a diameter of the channel (15) of the neck portion. Thus neither liquid in the reservoir nor suspended solids can reach the head and are subsequently not discarded when the head is removed.

Figure 3:
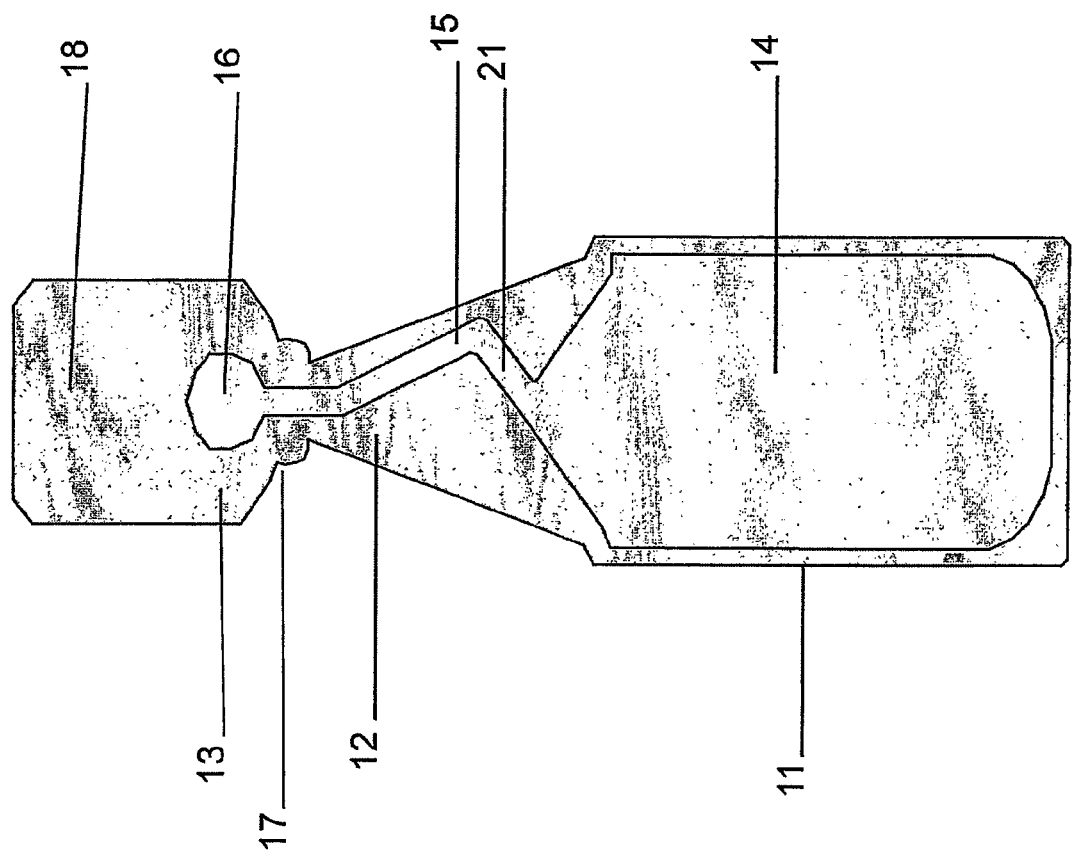
FIG. 3 shows a schematic cross-section of a further ampoule of the invention, again not showing the base portion.

Referring specifically to FIG. 3, a further trap is illustrated. The ampoule of FIG. 3 comprises a channel (15) including an L-bend (21). This forms a trap for settled suspension, preventing this from reaching the bulb when the ampoule is inverted or shaken.

Figure 4:
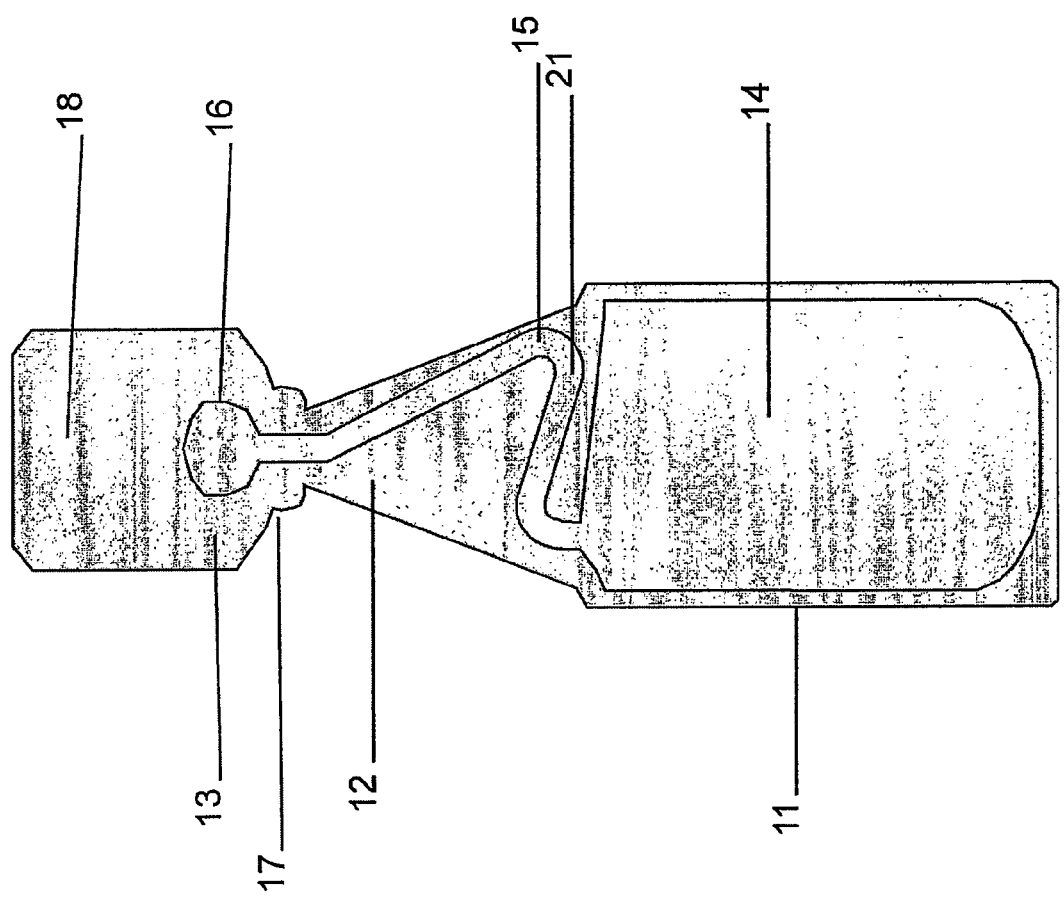
FIG. 4 shows a schematic cross-section of a further ampoule of the invention, again not showing the base portion.

Referring specifically to FIG. 4, a further trap is illustrated. The ampoule of FIG. 4 comprises a channel (15) with two bends, including a U-bend (21). This forms a trap for settled suspension, preventing this from reaching the bulb when the ampoule is inverted or shaken.

Figure 5:
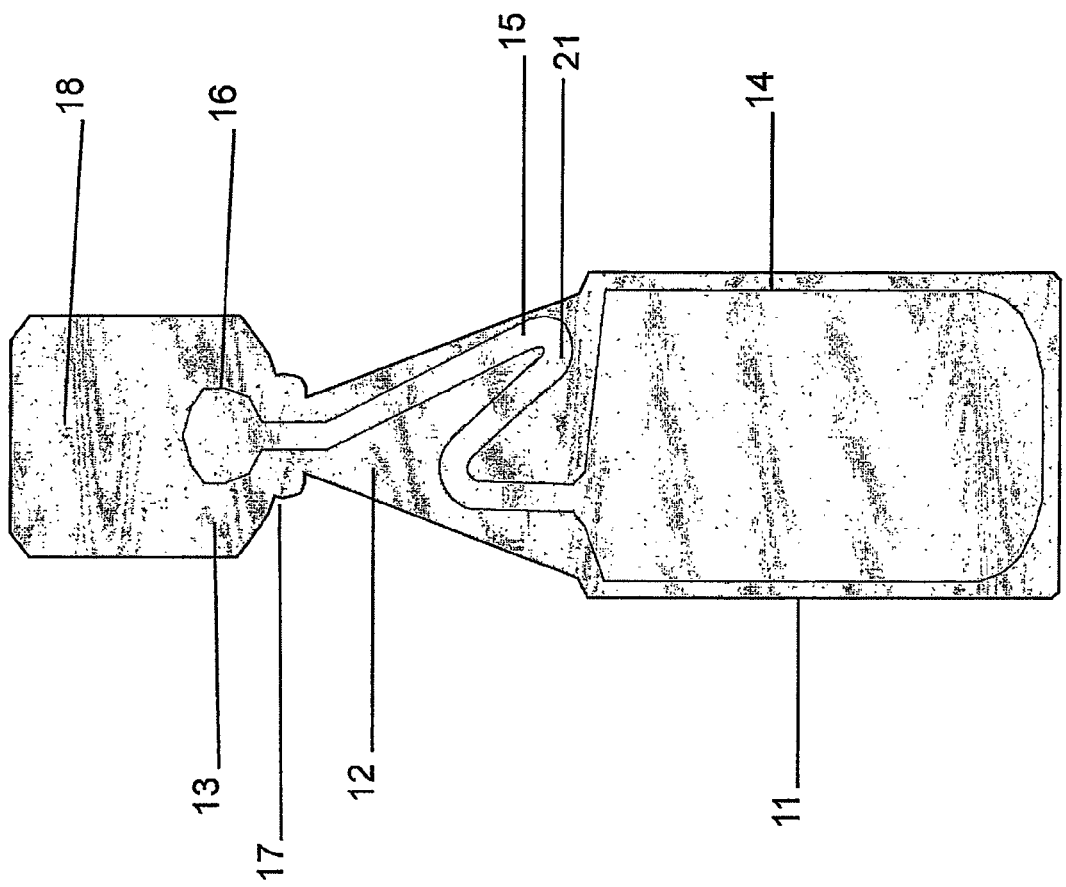
FIG. 5 shows a schematic cross-section of a further ampoule of the invention, again not showing the base portion.

Referring specifically to FIG. 5, a further embodiment of the trap of FIG. 4 is illustrated. The ampoule comprises a channel (15) with two bends, including a U-bend (21). This forms a trap for settled suspension, preventing this from reaching the bulb when the ampoule is inverted or shaken.

The present invention thus provides ampoules and methods of making them.

The invention claimed is:

1. An ampoule made of plastics material, comprising:
   a body comprising a reservoir containing up to 10 ml of a suspension of a pharmaceutical;
   a removable head portion comprising a bulb; and
   a neck portion linking the body to the head, comprising a channel through which liquid in the reservoir can exit the ampoule once the head has been removed,
   wherein the bulb is in fluid communication with the channel of the neck portion, and has a diameter greater than the diameter of the channel of the neck portion, and
   wherein the neck portion comprises a particulate trap which prevents solid material held in suspension in the liquid from settling in the part of said ampoule which is removed on opening, and wherein the particulate trap is formed by a U-bend in the channel of the neck portion.

2. The ampoule of claim 1, wherein the channel has a diameter of 3 mm or less.

3. The ampoule of claim 2, wherein the particulate trap additionally prevents liquid of the suspension from reaching the head.

4. The ampoule of claim 3, wherein the channel has a diameter of 2 mm or less.

5. The ampoule of claim 1, wherein the neck portion is of reduced diameter so that a combination of air in the head and surface tension prevents liquid from reaching the head.

6. The ampoule of claim 1, wherein the particulate trap comprises two U-bends.

7. The ampoule of claim 6, wherein the channel has a diameter of 3 mm or less.

8. The ampoule of claim 6, wherein the channel has a diameter of 2 mm or less.

9. An ampoule made of plastics material, comprising:
a body comprising a reservoir containing up to 10 ml of a suspension of a pharmaceutical;
a removable head portion comprising a bulb; and
a neck portion linking the body to the head, comprising a channel of 3 mm or less in diameter through which liquid in the reservoir can exit the ampoule once the head has been removed,
wherein the bulb is in fluid communication with the channel of the neck portion, and has a diameter greater than the diameter of the channel of the neck portion, and
wherein the neck portion comprises a trap which prevents both liquid and also solid material held in suspension in the liquid from settling in the part of said ampoule which is removed on opening, and wherein the particulate trap is formed by a U-bend in the channel of the neck portion.

10. An ampoule comprising:
a body comprising a reservoir for up to 50 ml of liquid;
a removable head portion comprising a bulb; and
a neck portion, linking the body to the head, comprising a channel through which liquid in the reservoir can exit the ampoule when the head has been removed,
wherein the bulb is in fluid communication with the channel of the neck portion, and has a diameter greater than the diameter of the channel of the neck portion, and
wherein the neck portion comprises a trap to prevent suspended particles in the liquid which have settled from reaching the head, and wherein the trap is formed by a bend of at least 90 degrees in the channel of the neck portion.

11. The ampoule of claim 10, wherein the channel has a diameter of 3 mm or less.

12. The ampoule of claim 11, wherein the trap additionally prevents liquid of the suspension from reaching the head.

13. The ampoule of claim 12, wherein the channel has a diameter of 2mm or less.

14. The ampoule of claim 10, wherein the neck portion is of reduced diameter so that a combination of air in the head and surface tension prevents liquid from reaching the head.

15. The ampoule of claim 10, wherein the trap is formed by two bends in the channel of the neck portion.

16. An ampoule comprising:
a body comprising a reservoir for up to 50 ml of liquid;
a removable head portion comprising a bulb; and
a neck portion, linking the body to the head, comprising a channel of 3 mm or less in diameter through which liquid in the reservoir can exit the ampoule when the head has been removed,
wherein the bulb is in fluid communication with the channel of the neck portion, and has a diameter greater than the diameter of the channel of the neck portion, and
wherein the neck portion comprises a trap to prevent suspended particles in the liquid which have settled from reaching the head, and wherein the trap is formed by two bends in the channel of the neck portion, both bends beings of 90 degrees or more.

* * * * *